United States Patent
Jean et al.

(10) Patent No.: US 10,274,436 B2
(45) Date of Patent: Apr. 30, 2019

(54) RADIOMETRIC SYSTEM AND METHOD FOR DETECTING ICE ACCUMULATION INSIDE AN OPERATING JET ENGINE

(71) Applicant: BAYLOR UNIVERSITY, Waco, TX (US)

(72) Inventors: Buford Randall Jean, Lorena, TX (US); Brandon Herrera, Waco, TX (US); Stephen T. McClain, Waco, TX (US)

(73) Assignee: BAYLOR UNIVERSITY, Waco, TX (US)

( * ) Notice: Subject to any disclaimer, the term of this patent is extended or adjusted under 35 U.S.C. 154(b) by 160 days.

(21) Appl. No.: 15/460,171

(22) Filed: Mar. 15, 2017

(65) Prior Publication Data

US 2018/0266969 A1    Sep. 20, 2018

(51) Int. Cl.
*G01N 22/04* (2006.01)
*F02C 7/30* (2006.01)
(Continued)

(52) U.S. Cl.
CPC .......... *G01N 22/04* (2013.01); *F01D 21/003* (2013.01); *F02C 7/30* (2013.01); *G01K 11/006* (2013.01);
(Continued)

(58) Field of Classification Search
CPC .... G01N 22/00; G01N 22/04; G01N 21/3581; G01N 21/3563
(Continued)

(56) References Cited

U.S. PATENT DOCUMENTS

| 7,176,696 B2 * | 2/2007 | Cerati | A24C 5/3412 |
| | | | 324/633 |
| 7,652,488 B1 * | 1/2010 | Lopatin | F02K 9/08 |
| | | | 324/637 |

(Continued)

FOREIGN PATENT DOCUMENTS

| WO | 2015/061557 A1 | 4/2015 |
| WO | 2015/061557 A9 | 4/2015 |

OTHER PUBLICATIONS

Goodwin et al., "Engine Preparation and Instrumentation for the Second Ice Crystal Engine Test at NASA PSL-3 Test Facility", American Institute of Aeronautics and Astronautics, Jun. 13-17, 2016, pp. 1-17.
(Continued)

*Primary Examiner* — Jermele M Hollington
*Assistant Examiner* — Taqi R Nasir
(74) *Attorney, Agent, or Firm* — Jackson Walker, LLP (57) ABSTRACT

The present invention provides a system and method of detecting the presence of a foreign substance, such as ice, in an air-flow path within an operating jet engine by providing one or more electromagnetic sensors that are tuned to receive electromagnetic waves at one or more frequencies generated by the operating jet engine that change upon the presence of the foreign substance. In at least one embodiment, the waves can be transmitted to the electromagnetic sensor through an electromagnetically transparent window in a wall of the jet engine. In at least another embodiment, the electromagnetic sensor can be coupled with a connector that penetrates an operating chamber in the jet engine to measure the electromagnetic parameters of one or more components from within the chamber of the jet engine. In some embodiments, the amount of ice or other foreign substances can be measured or estimated.

11 Claims, 5 Drawing Sheets

(51) Int. Cl.
*F01D 21/00* (2006.01)
*G01K 11/00* (2006.01)
*G01V 3/12* (2006.01)
*B64D 15/20* (2006.01)

(52) U.S. Cl.
CPC ............... *G01V 3/12* (2013.01); *B64D 15/20* (2013.01); *F05D 2220/323* (2013.01); *F05D 2270/096* (2013.01); *F05D 2270/708* (2013.01)

(58) Field of Classification Search
USPC .................. 324/640, 76.14, 250, 637, 76.56
See application file for complete search history.

(56) References Cited

U.S. PATENT DOCUMENTS

| | | | |
|---|---|---|---|
| 8,525,705 B1* | 9/2013 | Lopatin | F02K 9/08 250/358.1 |
| 2002/0153368 A1* | 10/2002 | Gardner | B29C 70/82 219/545 |
| 2010/0066386 A1* | 3/2010 | Dos Santos | G01N 22/04 324/640 |
| 2015/0115105 A1* | 4/2015 | Renno | B64D 15/20 244/134 F |
| 2015/0294086 A1* | 10/2015 | Kare | G06F 19/3481 705/3 |
| 2016/0373837 A1 | 12/2016 | Sobanski et al. | |

OTHER PUBLICATIONS

Artemov et al., "Water and Ice Dielectric Spectra Scaling at 0°C.", Ferroelectrics, 2014, pp. 158-165, vol. 466, issue 1.

Norris, "LED-Based Engine Core Ice Sensor Under Test", Aviation Week & Space Technology, Sep. 5, 2016, pp. 1-3.

San Miguel, E., International Search Report for International Patent Application No. PCT/US2018/022139, dated Aug. 30, 2018, European Patent Office.

De La Loma, A., Written Opinion for International Patent Application No. PCT/US2018/022139, dated Aug. 30, 2018, European Patent Office.

* cited by examiner

RADIOMETRIC SYSTEM AND METHOD FOR DETECTING ICE ACCUMULATION INSIDE AN OPERATING JET ENGINE

CROSS REFERENCE TO RELATED APPLICATIONS

Not applicable.

STATEMENT REGARDING FEDERALLY SPONSORED RESEARCH OR DEVELOPMENT

Not applicable.

REFERENCE TO APPENDIX

Not applicable.

BACKGROUND OF THE INVENTION

Field of the Invention

The disclosure generally relates a system and method of detecting or measuring the intrusion and adhesion of a foreign substance to operating equipment that can interfere with the operation of such equipment. More specifically, the disclosure relates to a system and method of detecting or measuring the intrusion and adhesion of a foreign substance, such as ice, on interior surfaces of an operating jet engine.

Description of the Related Art

The interior structure of a turbofan jet engine is a complex arrangement of components that causes air to be drawn into the engine, compressed and accelerated by high speed rotating fan blades, redirected and aligned by stationary vanes, and eventually mixed with fuel which is burned to supply the rotational energy and thrust needed to propel an airplane in flight. There are two air streams associated with turbofan operation. One air stream bypasses the fuel-burning turbine system and is forced from the rear of the engine by the rotating fan blades that are being driven by the fuel-burning section of the engine. A second air stream provides the air needed to burn the jet fuel and the mass needed to drive the engine turbine. The high temperature zone of the engine is in the interior of the fuel-burning turbine. The operating temperatures of the compressor stages of the engine are governed by the inlet air temperature and the laws of thermodynamics based upon the pressures and velocities inside the compressor.

When an airplane flies through a water cloud, the inlet fluid stream consists of air and water. If the cloud comprises ice, the inlet fluid stream is air and ice crystals. At some point within the compressor stages, the ice crystals can melt due to the temperature rise of the fluid stream caused by its increased pressure. It is possible, based upon the variations in pressures and velocities of the fluid as it moves through the engine, for the melted ice crystals to refreeze and accumulate on the interior surfaces of the engine, such as on the surfaces of the stator vanes or shrouds that hold the vanes in place or shrouds that surround the rotating compressor blades. This accumulated ice can block the movement of air through the engine such that insufficient air is present to burn the fuel required for engine operation. Without sufficient air, the engine will not produce power and can flame out completely. Alternatively, ice can form on or in the engine rotor section and can severely damage the rotor blades and associated components.

In March 2016, a Boeing 787 Dreamliner airplane experienced an unrecoverable engine failure, that is, the engine flamed out and could not be restarted until after landing. The failure was caused by the ingestion and accumulation of ice inside the compressor stages of the airliner's turbofan jet engine. This example of an extremely hazardous situation does not appear to be an isolated event. It has been reported that the problem exemplified by the above incident still occurred after many years of intense efforts by engine makers to prevent different types of shutdowns stemming from internal icing while cruising at much higher altitudes. Engine icing is a well-known problem and the subject of considerable research by the National Aeronautics and Space Administration (NASA) to identify the causes of icing and to develop strategies to either avoid or mitigate the dangerous effects.

A key factor missing in dealing with the problem is a suitable instrument or sensor for determining when an aircraft engine is experiencing ice ingestion. Until now there has been no reliable means to detect when ice is starting to accumulate within the compressor stages of a turbofan jet engine and hence no way to alert the pilot and other personnel to a potentially catastrophic engine failure or no means to trigger an automatic adjustment in the engine control inputs to mitigate the harmful effects of the icing process.

An ultrasound transducer sensing method has been proposed for detecting ice accumulation in the interior of an engine. An ultrasound sensor relies upon the propagation and reflection characteristics of high frequency sound waves. The propagation characteristics of an ultrasound sound wave are affected by temperature and pressure and, notably, by the movement of the propagation medium, among other factors. Extremely high frequency acoustic noise that is unrelated to the presence or absence of ice accumulation is continuously being produced by the moving components in a jet engine and by the fuel combustion operation. The extremely high acoustic noise and the other factors make the reliable application of an ultrasound transducer inside a turbofan jet engine problematic.

An LED visible light reflection sensor has also been proposed. The LED sensor achieves its detection capability by the change in the index of refraction of the material covering the lens of the sensor from that of air to ice. While the index of refraction can be a reliable way to detect ice, the ice needs to form on the lens in order for the sensor to work. Thus, the measurement zone is a very small area and it would be possible for significant ice to form elsewhere in the engine and not be detected.

Therefore, there remains a need for a system and method that can detect or measure the intrusion and adhesion of a foreign substance, such as ice, on interior surfaces of operating equipment, such as a turbofan jet engine, and further advantageously provide an indicator to mitigate the adverse effects of such substance.

BRIEF SUMMARY OF THE INVENTION

The present invention provides a system and method of detecting the presence of a foreign substance, such as ice, in an air-flow path within an operating jet engine by providing one or more electromagnetic sensors that are tuned to receive electromagnetic waves at one or more frequencies generated by the operating jet engine that change upon the presence of the foreign substance. In at least one embodiment, the waves can be transmitted to the electromagnetic sensor through an electromagnetically transparent window in a wall of a component of the jet engine. In at least another embodiment, the electromagnetic sensor can be coupled with a connector that penetrates an operating chamber in the jet engine to measure the electromagnetic parameters of one or more components from within the chamber of the jet engine. In some embodiments, the amount of ice or other foreign substances can be measured or estimated.

The present invention provides such a reliable and robust sensing capability. The electromagnetic sensor relies on the distinct differences in the electrical permittivity of air, metal, water, and ice to uniquely identify when ice begins to form on the surfaces inside an engine. Moreover, the novel application of the disclosed microwave radiometric sensing technique can provide a reliable and easily-processed signal that is generally unaffected by the complex structure of the interior of the engine or by the high-speed motion of the fluid stream or the engine's rotating components.

The present disclosure provides a system for electromagnetically detecting the presence of a foreign substance in an operating jet engine comprising: an electromagnetic path configured to provide variable electromagnetic energy from one or more components from within the operating jet engine; a radiometer sensor configured to receive the electromagnetic energy from within the operating jet engine; and an analyzer communicatively coupled with the radiometer sensor.

The present disclosure provides a method for electromagnetically detecting the presence of a foreign substance in an operating jet engine comprising: providing an electromagnetic path through an interior of an operating jet engine; measuring electromagnetic energy from the interior of the operating jet engine with a radiometer sensor; comparing the measured electromagnetic energy with at least one reference electromagnetic energy established for an operating condition; determining that a foreign substance is present; and, if present, indicating the presence of the foreign substance.

DETAILED DESCRIPTION

The Figures described above and the written description of specific structures and functions below are not presented to limit the scope of what Applicant has invented or the scope of the appended claims. Rather, the Figures and written description are provided to teach any person skilled in the art to make and use the inventions for which patent protection is sought. Those skilled in the art will appreciate that not all features of a commercial embodiment of the inventions are described or shown for the sake of clarity and understanding. Persons of skill in this art will also appreciate that the development of an actual commercial embodiment incorporating aspects of the present disclosure will require numerous implementation-specific decisions to achieve the developer's ultimate goal for the commercial embodiment. Such implementation-specific decisions may include, and likely are not limited to, compliance with system-related, business-related, government-related, and other constraints, which may vary by specific implementation or location, or with time. While a developer's efforts might be complex and time-consuming in an absolute sense, such efforts would be, nevertheless, a routine undertaking for those of ordinary skill in this art having benefit of this disclosure. It must be understood that the inventions disclosed and taught herein are susceptible to numerous and various modifications and alternative forms. The use of a singular term, such as, but not limited to, "a," is not intended as limiting of the number of items. Further, the various methods and embodiments of the system can be included in combination with each other to produce variations of the disclosed methods and embodiments. Discussion of singular elements can include plural elements and vice-versa. References to at least one item may include one or more items. Also, various aspects of the embodiments could be used in conjunction with each other to accomplish the understood goals of the disclosure. Unless the context requires otherwise, the term "comprise" or variations such as "comprises" or "comprising," should be understood to imply the inclusion of at least the stated element or step or group of elements or steps or equivalents thereof, and not the exclusion of a greater numerical quantity or any other element or step or group of elements or steps or equivalents thereof. The device or system may be used in a number of directions and orientations. The order of steps can occur in a variety of sequences unless otherwise specifically limited. The various steps described herein can be combined with other steps, interlineated with the stated steps, and/or split into multiple steps. Some elements are nominated by a device name for simplicity and would be understood to include a system or a section, such as a processor would encompass a processing system of related components that are known to those with ordinary skill in the art and may not be specifically described.

The present invention provides a system and method of detecting the presence of a foreign substance, such as ice, in an air-flow path within an operating jet engine by providing one or more electromagnetic sensors that are tuned to receive electromagnetic waves at one or more frequencies generated by the operating jet engine that change upon the presence of the foreign substance. In at least one embodiment, the waves can be transmitted to the electromagnetic sensor through an electromagnetically transparent window in a wall of the jet engine. In at least another embodiment, the electromagnetic sensor can be coupled with a connector that penetrates an operating chamber in the jet engine to measure the electromagnetic parameters of one or more components from within the chamber of the jet engine. In some embodiments, the amount of ice or other foreign substances can be measured or estimated.

Figure 1A:
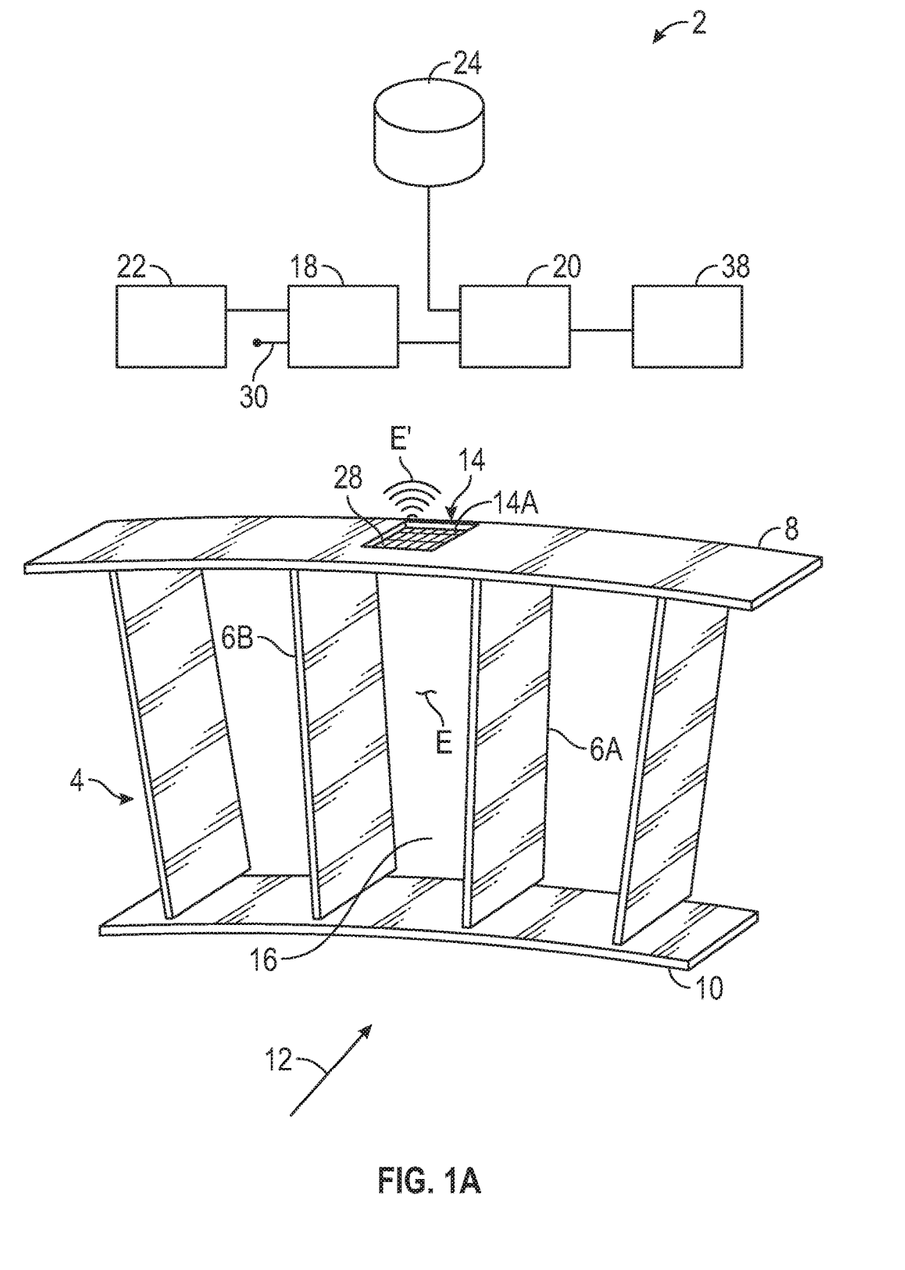
FIG. 1A is a schematic perspective view of an exemplary embodiment of the present invention.

FIG. 1A is a schematic perspective view of an exemplary embodiment of an electromagnetic sensor system according to the present invention. An electromagnetic sensor system 2 is electromagnetically coupled with a section of a stator 4 of a jet engine, such as a turbofan jet engine, where ice may form. The electromagnetic sensor system generally includes an electromagnetic path 14 from within the jet engine, such as from an inside chamber of the jet engine, a radiometer sensor 18 with an input port 30 to measure the electromagnetic radiation from the path, and an analyzer 20 to interpret the measurements. The analyzer 20 can provide results to an output interface 38 that may provide signals, alarms, controls, or other appropriate responses based on the results. In this embodiment, the electromagnetic path 14 can be through an electromagnetic transparent window 14A in a surface of a stator shroud 8 and positioned between two stator vanes 6A and 6B (generally, vanes 6) that are supported by a stator frame 10. However, the electromagnetic path 14 can be any path through which energy inside the engine can be sensed. The term "transparent" is meant to be interpreted broadly to include sufficient transmissibility that the sensed energy is not so obscured as to not be able to provide sufficient energy measurements to distinguish between an operating condition not having a foreign substance, such as an ice accumulation and one having the foreign substance.

One type of embodiment for the system 2 continuously compares the energy level emitted by the engine interior components to an energy that is emitted by a suitable reference source 22 that is communicatively coupled to, for example, the radiometer sensor 18. The energy emitted by the engine interior components can change depending on the fluid stream composition through the engine, that is, the composition of air, water, and any ice and any accumulation of ice in the engine. The change in energy can be measured by the radiometer sensor 18. Because the energy will naturally change with ambient and other conditions, a relative reference source 22 that measures various ambient conditions as an relative standard of reference, such as from outside the engine chamber, can be used as a comparison. The relative reference source 22 can be, for example and without limitation, a resistive load or a controlled noise source.

Alternatively or in addition to a relative reference source 22, a total power radiometer sensor 18 can be used and does not require a relative reference source. A total power radiometer sensor instead measures the input power to the sensor 18. The input power integrated over a period of time (that is, energy) can be compared to a predicted power level integrated over a known interval of time at various conditions, based on an analysis of the materials in the measurement zone and geometry of the measurement situation or compares the measured values to power levels measured under reference conditions. The predicted power levels can be contained, for example, in a database 24 for look up and correlation to an operating condition, such as may indicate whether the fluid stream composition is air, water, ice crystals and combinations, and/or an ice accumulation is likely to occur or has occurred.

A compressed and accelerated fluid stream 12 of air, and in some cases water and/or ice, passes between the vanes 6 of the stator 4. The purpose of the stator vanes 6 is to redirect the flow of the fluid stream 12 to present the proper flow characteristics of the fluid to the next stage of the engine, either another compression stage or to the combustion stage. Whenever the fluid flow path between the stator vanes 6 is free from accumulated ice, the flow of the fluid stream 12 is normal and the engine combustion stage receives sufficient air for the burning of the jet fuel. However, accumulated ice can restrict air flow, leading to the potential issues described above.

An underlying principle of the present invention is that air, water, and ice each have unique electromagnetic properties that can be measured with an electromagnetic sensor. A radiometer sensor 18 can be used to measure the emission of electromagnetic energy from a body of material based upon the material's temperature and its emissivity. A radiometer sensor 18 has the further advantage that its operation is not influenced by the movement of the compressor blades within or the flow rate of the air/fluid stream through the engine, unlike a sensor of almost any other type. In some cases, ice can form in the rotor section of the engine. A properly configured radiometer sensor system can measure the emitted radiation from the rotor sections, as well as from the stator sections or other portions of the engine, to provide a sensor having superior ice ingestion detection and measurement capability.

A dry engine will emit a different energy level from that of an engine that has ingested water, such as one flying through a cloud or rain, which will also differ significantly from the energy that is emitted by an engine that is experiencing ice accumulation. The characteristics of the radiometer sensor can be adjusted to maximize the sensitivity of the sensor to the hazardous ice and to distinguish the energy level emitted by the ice from the various energy emissions that are experienced through normal operation without causing a false alarm condition to be indicated. Among the important receiver characteristics that may be selected are the center frequency of operation, the receiver detection bandwidth, and the integration or averaging time, among others.

Microwave radiometers are well-known as remote sensing instruments that have been operated in such diverse applications as that of radio telescopes used to measure the extremely weak levels of energy that are impinging upon the earth from outer space, to the detection of sea ice floating in the ocean as observed from a spacecraft platform. The design and construction of a microwave radiometer includes an input port, such as a high gain antenna that the instrument uses to capture the input energy that is measured to produce a so-called antenna brightness temperature based upon the electromagnetic energy impinging upon the antenna from a distant target. A typical instrument design requires a highly controlled and stable internal temperature for all of the electronic components making up the radiometer sensor and the careful selection of an operating frequency protected from other sources of radiation such as from radars, communication systems, or stray sources of energy produced by industrial or scientific instruments and the like. Radiometer sensors, such as a Dicke-type radiometer sensor, have also required that a highly stable reference load or noise generator be used as a calibration standard to quantify the energy levels making up the brightness temperature of a remotely located object.

The electromagnetic sensor system 2 that is envisioned to be employed for the jet engine issue is applied in a setting for which extraneous energy is not likely to be present, nor is the reference energy level required to be stable and highly controlled, although such a system is certainly possible and is contemplated as an option for the present invention. According to the teaching of one embodiment of the present invention, the reference energy source is preferably located as close as possible to the energy transfer path or microwave transparent window communicating into the interior portion of the operating jet engine so as to provide a differential measurement for comparing engine radiated energy emissions. If the reference source is responsive to the temperature of the interior of the engine or relatable in a known way, it then will have an energy content that will track in proportion to the internal temperature of the engine.

A reasonable choice for the operating frequency, or more properly the operating bands of frequencies, of the engine ice radiometer sensor system is in the microwave spectrum, although other frequency bands could be used. It has been observed that a band of frequencies having a center frequency near 10 GHz offers the benefit of providing easy discrimination of the emission levels produced by a dry engine versus a wet engine versus an engine with accumulated ice. According to the Rayleigh-Jean's approximation to Planck's radiation law, the power levels emitted by an object can be expressed in terms of a brightness temperature, TB, which is given by the product of the physical temperature, T, of the body multiplied by a factor called the emissivity, $\epsilon$. The emissivity value for an object is a function of the constitutive electrical properties of the object, the polarization of the energy being observed, the angular orientation from which the energy is observed (generally, the angle between the direction that is normal to the surface and the direction of the propagation vector), and the geometry of the radiating object. According to radiometer theory, the value of the emissivity of a radiating body is equal to the object's power absorption coefficient; otherwise thermal equilibrium could not be achieved.

The electrical properties of metal, water, and ice are such that their emissivities are distinct. The emissivity of dry metals is almost zero owing to the high conductivities of metals. Water has a much lower emissivity than ice due to its high permittivity. The conductivity of water can also affect its emissivity. Based upon its lower electrical permittivity, the emissivity of ice is substantially larger than both liquid water and metal. During the operation of a jet engine at high altitudes or elsewhere, the internal temperatures of the compressor stages will often be near zero degrees Celsius and will not vary by a significant amount when ice accumulation may be a threat to the safe operation of the engine. As a consequence, the microwave brightness temperature of the internal components and the air flowing through the engine will be determined primarily by the emissivity value as influenced by the presence of water or ice. The microwave brightness temperature inside the engine will appear to increase significantly due to the formation of ice. The fact that emissivity will be a controlling variable for determining the microwave energy emissions means that a microwave radiometer can be an effective and reliable sensor to measure the accumulation of ice inside an operating jet engine.

In general, the system and method uses an electromagnetic path 14 that is electromagnetically transparent or otherwise communicates with the interior region of an operating turbofan jet engine. One non-limiting example of such a path is a microwave frequency electromagnetically transparent window 14A that includes a small opening in the metal of the stator shroud 8 around the stator vanes 6 (or through other components of the jet engine). The opening of the window can be filled and sealed by a suitable dielectric material 28, such as a ceramic material, having temperature and physical strength properties that do not adversely affect the performance or reliability of the jet engine.

The window 14A electromagnetically communicates with a passage 16 created by the bottom and top surfaces of the stator shroud 8 and frame 10 and the two vanes 6, including the metals from which the structure is constructed. Energy E is dispersed in this opening and can be sensed through the window. The window is positioned so as to provide a path for a radiated energy E' portion to be sensed by the radiometer sensor 18, including energy emitted from interior surfaces of the engine with any accumulated ice adhering to the surfaces. The energy can be measured through an appropriately designed measurement input port 30, such as an antenna, of the radiometer sensor 18. For example, the radiometer sensor can be a Dicke-type, total power, and other types of radiometers. After the energy E' is sensed by the radiometer sensor, the information can be communicated to an analyser 20 for interpretation and correlation to the operating condition of the engine and provide to the output interface. If appropriate, the output interface 38 can provide a signal or alarm to indicate the operating condition, automatically exercise some control over the operation of the engine to mitigate the condition, or provide other output. The analyzer can provides results to the output interface 38 for some action such as a signal, an alarm, control, or other operation.

The electromagnetic properties of the material 28 used to fill the opening of the window 14A and the design of the opening to establish the window as an electromagnetic path to the radiometer sensor are important features for the proper operation of the sensor for ice accumulations. The electromagnetically transparent window 14A is designed with a size and shape to permit electromagnetic waves of the chosen operating frequency to couple to the input port 30 of the radiometer sensor 18 with low loss and low reflection. In at least one embodiment, the window behaves as a waveguide having a rectangular, circular, or other suitably chosen cross-sectional shape, such that window will have a cutoff frequency below which energy of a given propagation mode will not be allowed to pass. For such a window as a waveguide, there is a minimum dimension that depends upon the operating frequency and the electromagnetic properties of the material that fills the window through which energy can be passed. There can be some advantage to selecting a window size that is larger than the minimum size required for the lowest, or dominant, mode of propagation, limited by structural and design requirements of the engine. If the size of the window, the material filling the guide, and the operating frequency are chosen such that multiple modes of propagation can exist in the window, the efficiency of energy collection into the input port of the radiometer sensor can sometimes be increased. This efficiency is counter intuitive to typical waveguide designs that are used for applications such as communication or radar systems, because higher order modes typically create distortion. In this application, the multiple modes can be used to collect additional energy input.

The electromagnetically transparent window as a waveguide can be filled with a suitable low-loss material and have a shape to provide low reflection of energy that enters the window 14A and be communicated to the input port 30 and be an effective impedance match over the desired operating bandwidth. The design of low-loss and well-match coupling structures is a common requirement for microwave and radio frequency systems and will be well understood by those skilled in the art.

Figure 1B:
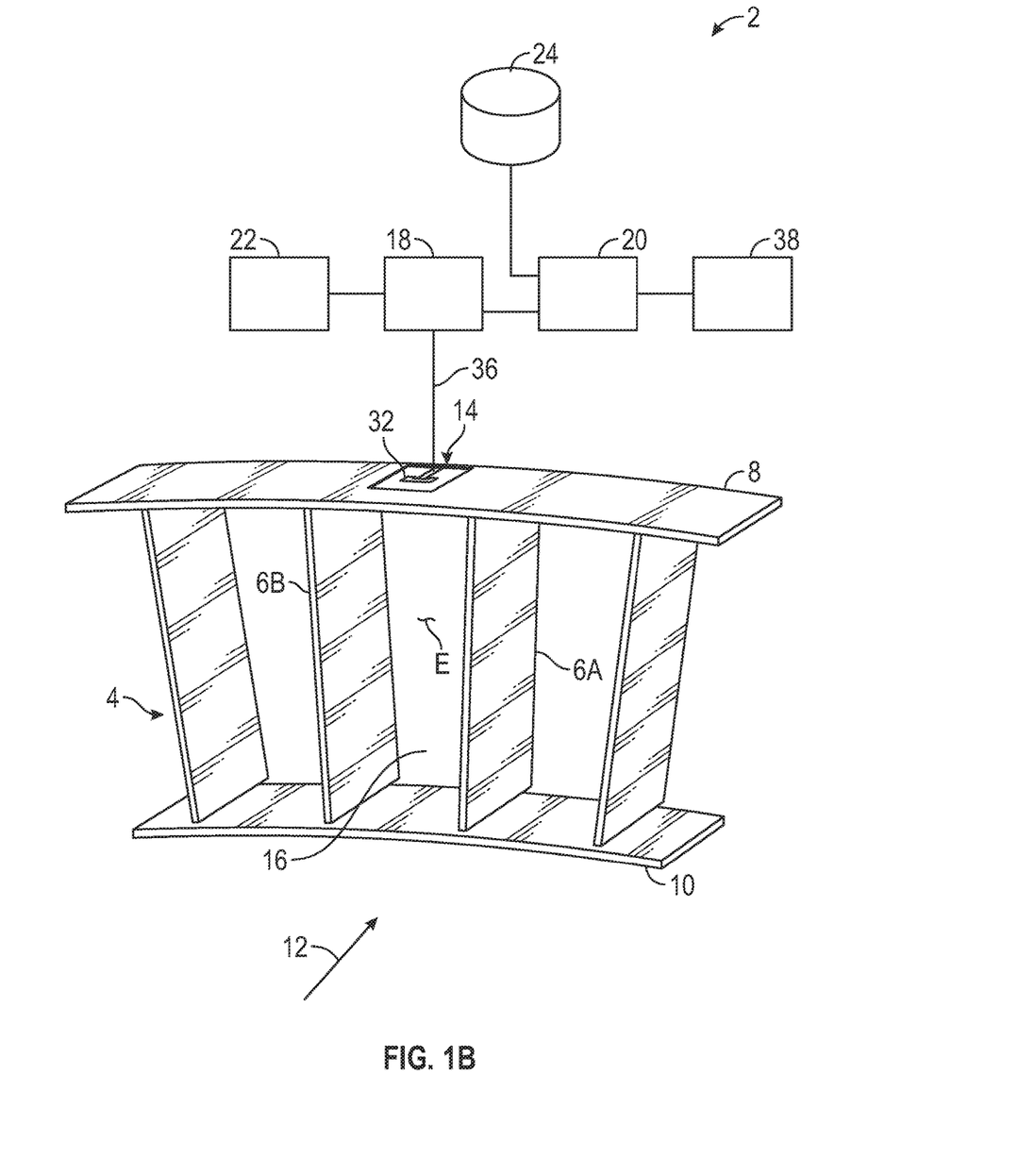
FIG. 1B is a schematic perspective view of an exemplary embodiment of the present invention.

FIG. 1B is a schematic perspective view of another exemplary embodiment of an electromagnetic sensor system according to the present invention. As in FIG. 1A, an electromagnetic sensor system 2 is electromagnetically coupled with a section of a jet engine stator 4. The sensor system 2 generally includes an electromagnetic path 14, a radiometer sensor 18 with an input port 30 to measure the electromagnetic radiation from the path, and an analyzer 20 to interpret the measurements. The analyzer 20 can provide results to an output interface 38 that may provide signals, alarms, controls, or other appropriate responses based on the results. The figure illustrates an electromagnetic path 14 established independent of the window 14A through the stator shroud 8 that was described in FIG. 1A. An electromagnetic coupling component 32, such as a patch antenna or planar coupling component, can be mounted within the operating jet engine, such as in the stator shroud 8 (instead of a window), and coupled to the input port 30 of the radiometer sensor 18 through a connector 36, such as coaxial cable, that penetrates the chamber. Design options for a patch antenna and the like are readily available, and it will be recognized by those skilled in the art that various conductor shapes can be selected to give the energy coupling characteristics necessary for the desired radiometer operation, which again requires low losses and low reflection.

In addition to planar structures, there is the option of establishing the path 14 through a probe or coupling loop structure that can effectively communicate electromagnetic energy from various portions of the engine chamber interior into the input port 30 of the radiometer sensor 18. Probe and loop structures are further contemplated which cause the stator vane structure itself to behave as a wave guiding element for enhanced energy recovery efficiency from the interior regions of the engine, as would be known to those skilled in the art given the teachings herein.

As described in FIG. 1A, the measured electromagnetic energy can be compared with at least one reference electromagnetic energy established for an operating condition. One type of embodiment for the system compares the energy level emitted by the engine interior components to an energy that is emitted by a suitable reference source 22 that is communicatively coupled to, for example, the radiometer sensor 18. Alternatively or in addition to a relative reference source 22, a total power radiometer sensor 18 can be used and does not require a relative reference source. A total power radiometer sensor 18 measures the input power to the sensor. The input power integrated over a period of time (that is, energy) can be compared to a predicted power level integrated over a known interval of time at various conditions, The predicted power levels can be contained, for example, in a database 24 for look up and correlation to an operating condition, such as may indicate whether the fluid stream composition is air, water, ice crystals and combinations, and/or an ice accumulation is likely to occur or has occurred.

Figure 2:
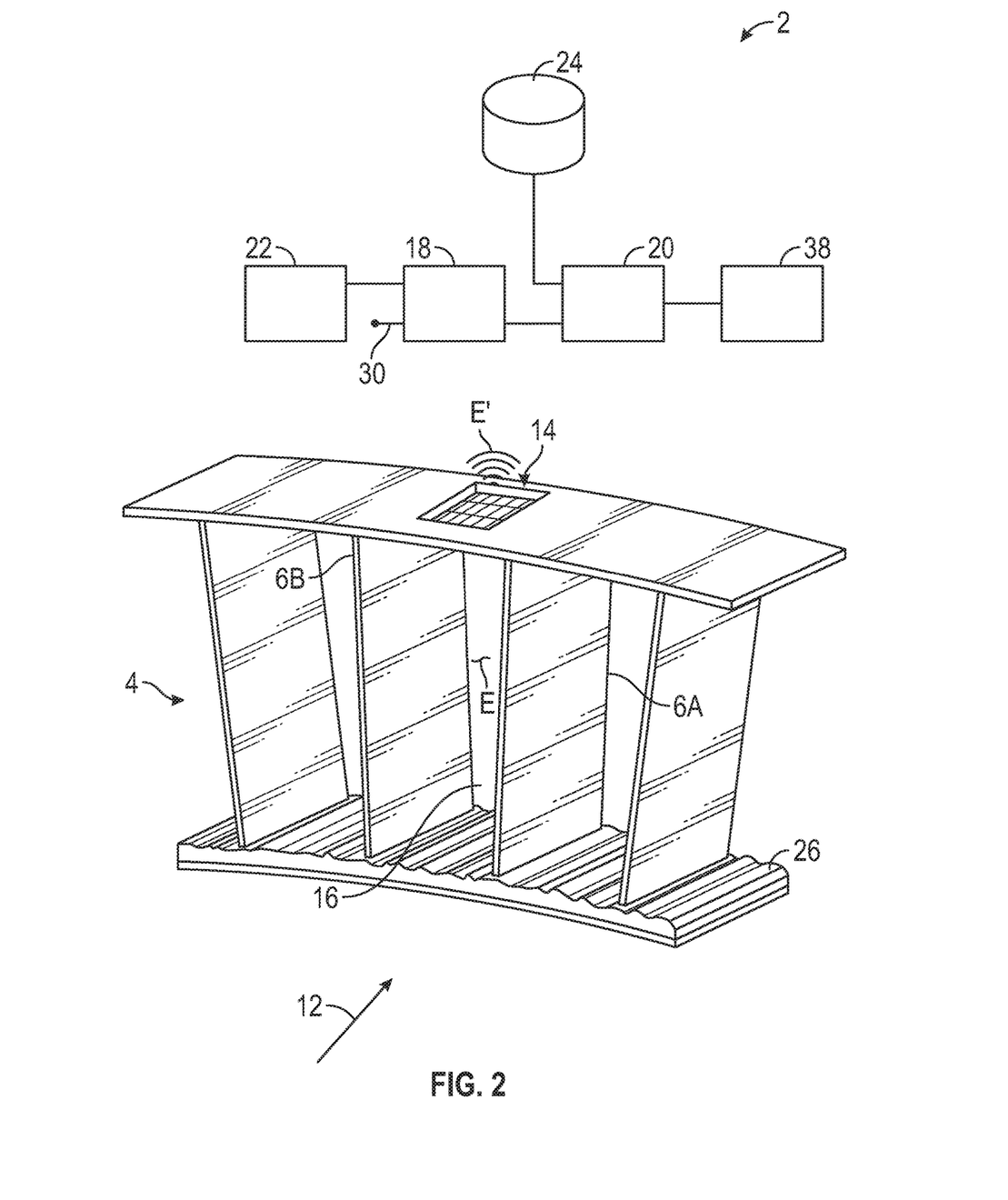
FIG. 2 is a schematic perspective view of FIG. 1A with an exemplary foreign substance accumulation, such as ice.

FIG. 2 is a schematic perspective view of FIG. 1A with an exemplary foreign substance accumulation, such as ice. FIG. 2 shows the accumulated ice on one of the surfaces of the stator, such as on the stator frame 10. The accumulation might occur when ice crystals are ingested into the engine, melt, and then refreeze in the stator stage. The location of the ice crystals as shown is exemplary of the possible locations of ice formation and the operation of the sensor is not limited by the exact location of the ice. The ice accumulation 26 can restrict the fluid flow path. The ice accumulation can form on various surfaces of the stator 4 and other surfaces of the engine and alters the flow of the fluid stream 12. Sufficient ice accumulation can significantly reduce the total air mass flow through the engine to the point at which the engine combustion stage is unable to burn the fuel required to maintain engine operation and thrust. If the presence of ice accumulation 26 can be identified by the electromagnetic sensor system 2 described above before the ice grows to the point of restricting the fluid steam 12, preventative action can be taken to adjust the controls of the engine to cause the freezing point to move to a different location within the compressor.

The ice can accumulate at other locations throughout the engine. The described location of the stator is for exemplary nonlimiting purposes. It is contemplated that the electromagnetic sensor system 2 can be used in multiple locations throughout the engine to monitor conditions of the engine, and advantageously provide output of such conditions for possible corrective action, if appropriate.

For some embodiments of the sensor and application of the sensing method contemplated according to the present invention, it may be useful to provide measurements at two or more distinct frequency bands. Multiple bands may advantageously take advantage of differing frequency dependent properties of the emitted energy that can be created by the frequency dependent emissivity characteristics of the air or water or ice fluid streams or by the frequency dependent radiation and emission characteristics associated with the specific geometry of an individual engine interior design or construction. The multiple levels can add a level of discrimination between the sensed energy signatures that may be used for greater accuracy and more precise definition of the engine operational conditions. Multiple bands can also provide a measure of redundancy for added safety should an interfering signal be present affecting one of the measurement bands.

Flexibility in frequency band selection can allow for optimizing the sensitivity and reliability of the sensor to accommodate various features that may be introduced by different engine manufacturers or allowing the operation of the sensor to be adjusted during differing flight regimes. It is anticipated that the number and location of the various possible sensing points within the engine and the frequencies of operation can be useful design options for a given engine type or expected operating regime, as will be appreciated by those skilled in the art of applying electromagnetic frequency sensors and systems.

Figure 3:
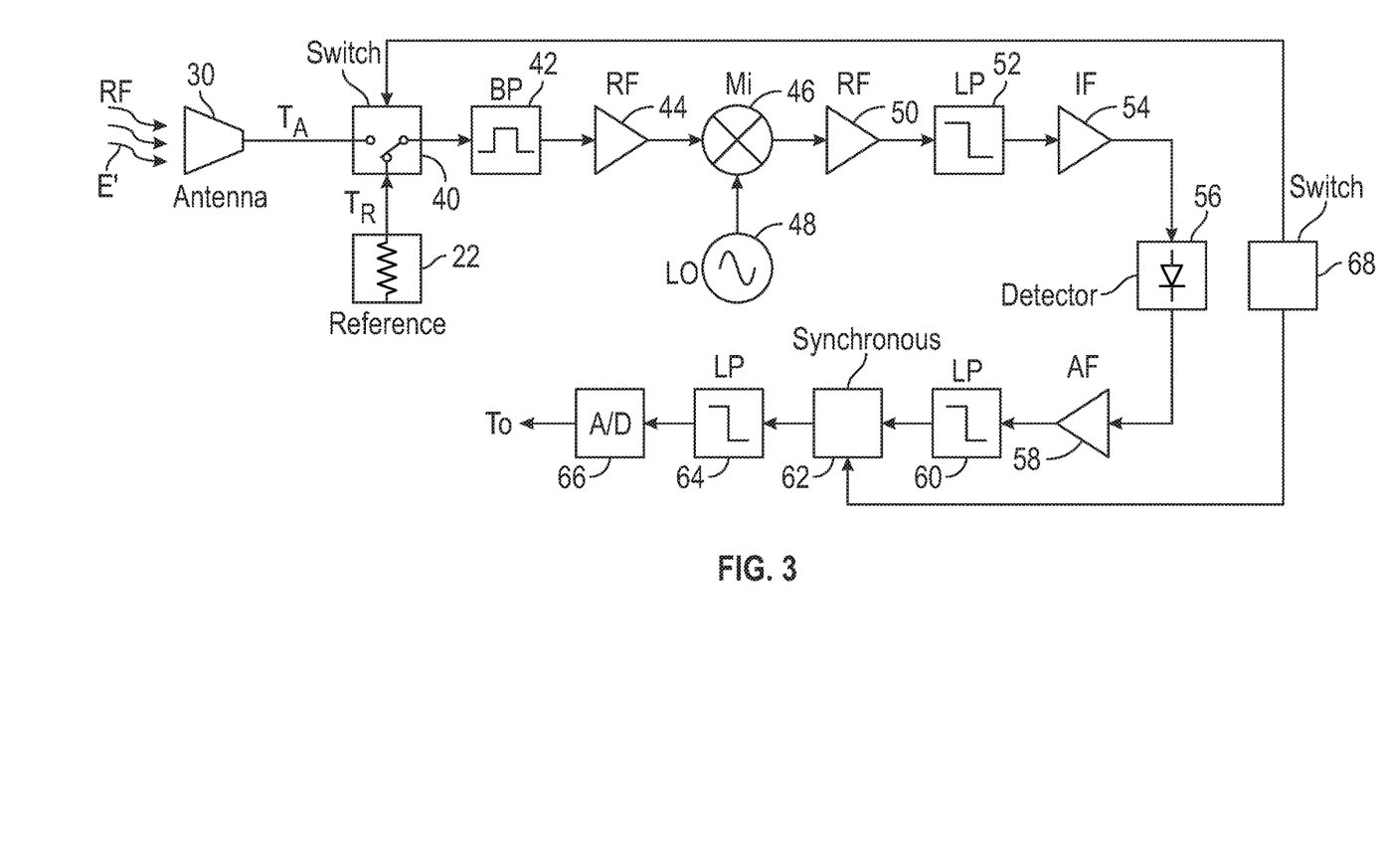
FIG. 3 is a block diagram of an exemplary radiometer sensor system according to the present invention.

FIG. 3 is a block diagram of an exemplary radiometer sensor system according to the present invention. FIG. 3 depicts the collection of energy E' passing through the transparent window 14A shown in FIGS. 1A and 2 and the location of a reference source 22 as reference input, whose energy emission is proportional to the temperature of the engine's interior components. (The embodiment for FIG. 1B is similar, but relies on the connector 36 rather than input port 30 as an antenna.) This exemplary embodiment of the radiometer receiver includes a switch 40, controlled by switch controller 68, which alternately connects the sensor port from the input port 30, such as an antenna, of the sensor 18 and the reference source 22 to the input port of the sensor 18. Other exemplary sensor system components can include a bandpass filter 42, low noise input amplifier 44, frequency shifting mixer 46, radio frequency (RF) amplifier 50, intermediate frequency (IF) band limiting filter 52, IF amplifier 54, detector circuit 56, low frequency amplifier 58, lowpass filter 60, synchronous detector circuit 62, lowpass filter or integrating circuit 64, and an analog-to-digital converter 66. The local oscillator 48 sets the center frequency of the measurement band.

Figure 4:
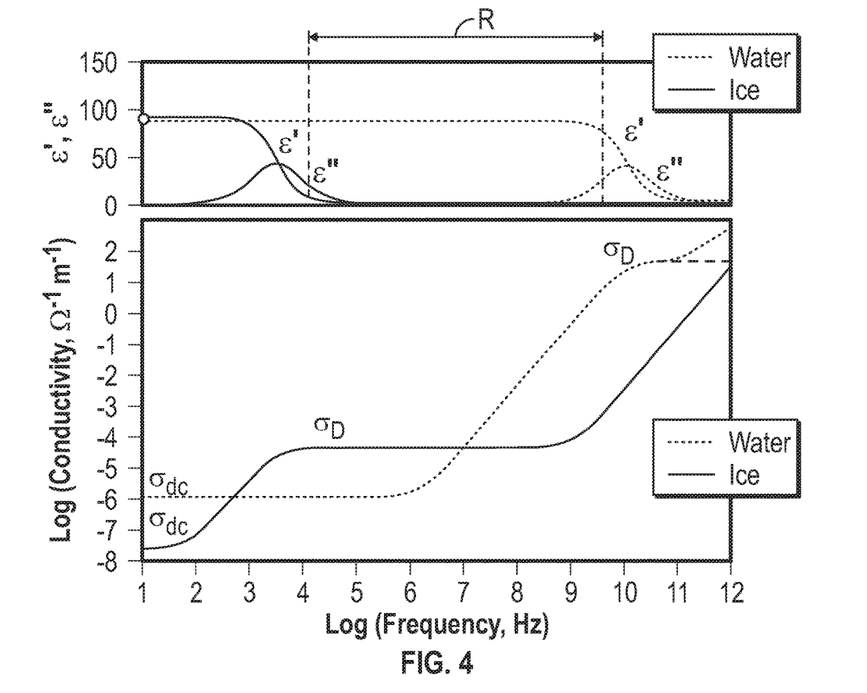
FIG. 4 is a graph of the electrical properties, namely the complex electrical permittivity, of both liquid water and ice at temperature near 0° C.

FIG. 4 is a chart of two graphs of the electrical properties of both liquid water and ice at temperature near 0° C. The electrical properties include the complex electrical permittivity (upper graph) and the electrical conductivity (lower graph), which is also a component of the imaginary part of the total complex permittivity. The X-axis is the frequency expressed in a logarithmic scale of Hz. The Y-axis of the lower graph is the conductivity expressed in a logarithmic scale of $ohm^{-1}$-$meter^{-1}$. The Y-axis of the upper graph shows both the real part of permittivity ($\epsilon'$) and the imaginary part of permittivity ($\epsilon''$). The dielectric spectra of water and ice show that the complex permittivities and the electrical conductivities of water and ice are significantly distinct from each other in the range marked as "R" in FIG. 4, namely between about logarithmic frequency range from 4.0 to 9.5. Thus, operating in this range will advantageously assist in discriminating energy emitted by the water and ice.

Experiment 1

Figure 5:
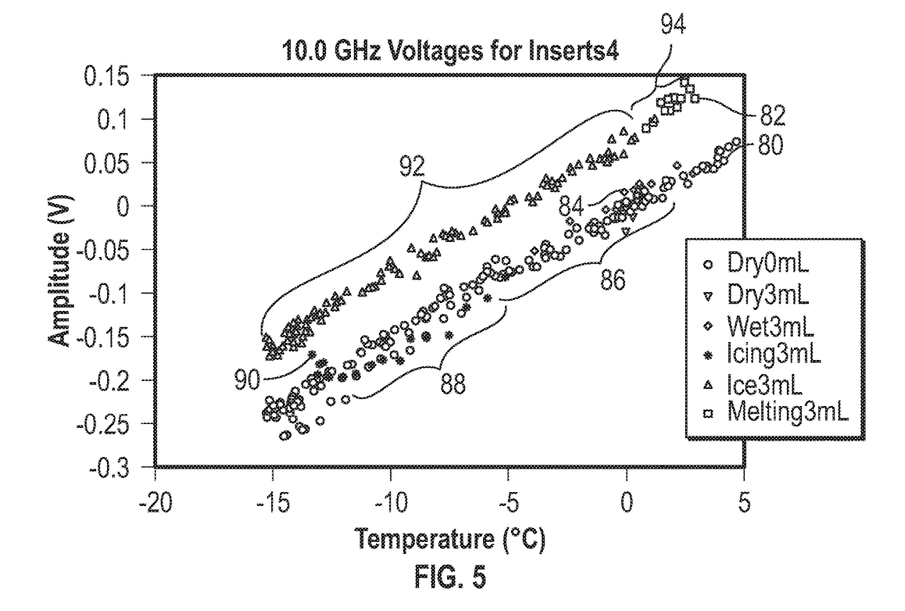
FIG. 5 is a graph of the measured temperature energy collected by the radiometer sensor for a series of tests simulating dry, wet, and ice-coated conditions on a stator stage segment of an operating turbofan jet engine.

FIG. 5 is a graph of the measured temperature energy collected by the radiometer sensor for a series of tests simulating dry, wet, and ice-coated conditions on a stator stage segment of an operating turbofan jet engine. FIG. 5 shows the results in tests that mimic the behavior of a stator stage segment of a turbofan jet engine operating under various conditions. The X-axis represents a temperature in Celsius, and the Y-axis represents an amplitude of voltage directly proportional to the measured temperature energy as electromagnetic energy. The lower curve 80 largely represents dry air and the upper curve 82 represents frozen moisture as ice. The differences in detected emissivities are apparent and support the ability of a sensor to distinguish between dry air, water, and ice in the simulated stator portion of a jet engine.

More specifically, a test apparatus simulated a dry stator portion of a jet engine and emitted energy recorded between −15° C. to 5° C. After the readings were obtained for the dry assembly, an access port was opened and 3 ml of water was placed in the stator assembly at about 0° C. shown at zone 84. The temperature rose briefly due to the opened port and then decreased through zone 86 until the water began to freeze at about −6° C. in zone 88. At about −12° C., the freezing water became ice and the energy moved from the curve 80 to the curve 82, shown at zone 90. Once converted to ice, the emissivity energy followed the curve 82 in zone 92 at a distinctly higher emitted energy than the curve 80 for a given temperature. At 0° C. and warmer, the ice in curve 82 started to melt through zone 94.

Other and further embodiments utilizing one or more aspects of the inventions described above can be devised without departing from the disclosed invention as defined in the claims. For example, other bands beside microwave can be used depending on the sensitivity of the radiometer sensor, operating conditions, energy emitted, and other factors. The location of the electromagnetic path can vary and the numbers of electromagnetic paths, sensors, antennas, and other components can vary. The components described herein can be separate or combined with other components. Other variations can occur in keeping within the scope of the claims.

The invention has been described in the context of preferred and other embodiments and not every embodiment of the invention has been described. Obvious modifications and alterations to the described embodiments are available to those of ordinary skill in the art. The disclosed and undisclosed embodiments are not intended to limit or restrict the scope or applicability of the invention conceived of by the Applicant, but rather, in conformity with the patent laws, Applicant intends to protect fully all such modifications and improvements that come within the scope or range of equivalents of the following claims.

What is claimed is:

1. A system for electromagnetically detecting the presence of a foreign substance in an operating jet engine comprising, comprising:
    an electromagnetic path configured to provide variable electromagnetic energy from one or more components from within the operating jet engine;
    a radiometer sensor configured to receive the electromagnetic energy from within the operating jet engine; and
    an analyzer communicatively coupled with the radiometer sensor.

2. The system of claim 1, wherein the electromagnetic path comprises an opening forming in a component of the operating jet engine.

3. The system of claim 2, further comprising filling the opening with an electromagnetic transparent material.

4. The system of claim 3, wherein the electromagnetic transparent material comprises a dielectric material.

5. The system of claim 1, wherein the electromagnetic path comprises an antenna coupled inside the operating jet engine.

6. The system of claim 5, wherein the antenna is in communication with a fluid stream through the jet engine.

7. The system of claim 1, further comprising a reference source coupled to the radiometer sensor, the analyzer, or a combination thereof and configured to provide a reference energy to provide a differential energy with the variable electromagnetic energy from within the engine to determine operating conditions of the engine.

8. The system of claim 1, wherein the radiometer sensor comprises a total power radiometer configured to measure power to the operating jet engine and the system further comprises at least one predicted power level for a given operating condition of the jet engine for comparison with the measured power.

9. A method of electromagnetically detecting the presence of a foreign substance in an operating jet engine, the method comprising:
    providing an electromagnetic path through an interior of an operating jet engine;
    measuring electromagnetic energy from the interior of the operating jet engine with a radiometer sensor; and
    comparing the measured electromagnetic energy with at least one reference electromagnetic energy established for an operating condition;
    determining that a foreign substance is present; and
    if present, indicating the presence of the foreign substance.

10. The method of claim 9, wherein comparing the measured electromagnetic energy with at least one reference electromagnetic energy established for an operating condition comprises comparing with a relative reference source on at least an intermittent basis.

11. The method of claim 9, wherein comparing the measured electromagnetic energy with at least one reference electromagnetic energy established for an operating condition comprises comparing with previously determined electromagnetic energies at various operating conditions.

* * * * *